United States Patent [19]

Morini et al.

[11] Patent Number: 5,468,704
[45] Date of Patent: Nov. 21, 1995

[54] COMPONENTS AND CATALYSTS FOR THE POLYMERIZATION OF OLEFINS

[75] Inventors: Giampiero Morini, Voghera; Enrico Albizzati, Arona; Umberto Giannini; Raimondo Scordamaglia, both of Milan; Luisa Barino, Novara, all of Italy

[73] Assignee: Montell North America Inc., Wilmington, Del.

[21] Appl. No.: 315,747

[22] Filed: Sep. 30, 1994

[30] Foreign Application Priority Data

Oct. 1, 1993 [IT] Italy .................. MI93A2102

[51] Int. Cl.⁶ .................. B01J 31/02; B01J 31/38
[52] U.S. Cl. .................. 502/115; 502/116; 502/118; 502/125; 502/127; 502/133
[58] Field of Search .................. 502/115, 116, 502/118, 125, 127, 133

[56] References Cited

U.S. PATENT DOCUMENTS

| | | | |
|---|---|---|---|
| 4,522,930 | 6/1985 | Albizzati et al. | 502/124 |
| 4,540,680 | 9/1985 | Speca | 502/119 |
| 5,068,213 | 11/1991 | Albizzati et al. | 502/126 |

FOREIGN PATENT DOCUMENTS

| | | |
|---|---|---|
| 0039971 | 11/1981 | European Pat. Off. . |
| 0361494 | 4/1990 | European Pat. Off. . |
| 0407808 | 1/1991 | European Pat. Off. . |

| | | |
|---|---|---|
| 61-231008 | 10/1986 | Japan . |

OTHER PUBLICATIONS

Bracke et al. "Chemistry of the S=O Bond . . . " J. Chem. Soc. Perkin Trans. 2 (7), pp. 912–923. 1989.

Primary Examiner—E. Rollins Cross
Assistant Examiner—Timothy H. Meeks

[57] ABSTRACT

Disclosed is a catalyst for the polymerization of olefins, which includes the product of the reaction between an Al-alkyl compound and a solid catalyst component containing a magnesium halide in active form, a titanium compound and an electron-donor selected from the 1,3-diketones of formula:

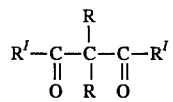

wherein the radicals R are the same or different, the radicals R′ are the same or different, and R and R′ are $C_1$–$C_{20}$ alkyl, $C_3$–$C_{20}$ cycloalkyl, $C_6$–$C_{12}$ aryl, $C_7$–$C_{20}$ arylalkyl or alkylaryl radicals or hydrogen, with the proviso that at least one of the R radicals is not hydrogen and can be bonded with the other R radical to form a cyclic structure, and at least one of the R′ radicals, which are not bonded to one another to form a cyclic structure, is a branched alkyl, cycloalkyl or aryl radical, or is bonded to one or both R radicals to form a cyclic structure.

8 Claims, No Drawings

COMPONENTS AND CATALYSTS FOR THE POLYMERIZATION OF OLEFINS

The present invention relates to a solid catalyst component comprising an electron-donor selected from a particular class of diketones, and to a catalyst for the polymerization of $CH_2=CHR$ olefins, Wherein R is hydrogen or a $C_1-C_6$ alkyl radical or an aryl radical, comprising the product of the reaction between said solid catalyst component, an Al-alkyl compound and, optionally, an electron-donor compound.

Catalysts comprising titanium compounds supported on magnesium halides in active form are well known in the art.

Catalysts of this type are described, for example, in U.S. Pat. No. 4,298,718. Said catalysts, although very active in the polymerization both of ethylene and of α-olefins, such as propylene, are not sufficiently stereospecific.

Stereospecificity has been improved by adding an electron-donor compound to the solid component comprising the titanium compound (U.S. Pat. No. 4,544,717).

Further improvements have been obtained by using both an electron-donor compound added to the solid catalyst component (internal donor) and one added to the Al-alkyl compound (external donor; U.S. Pat. No. 4,107,414).

Extremely high performances, both in terms of activity and stereospecificity, are given by the catalysts described in European Patent 0045977. Said catalysts comprise as a solid catalyst component a magnesium halide in active form on which is supported a titanium halide ($TiCl_4$) and an electron-donor compound selected from specific classes of carboxylic acid esters, such as the phthalates, for example. The co-catalyst used is an Al-alkyl compound to which is added a silicon compound containing at least one Si—OR bond (R=hydrocarbon radical).

U.S. Pat. No. 4,522,930 describes catalysts whose solid catalyst component is characterized in that it contains an electron-donor compound which is extractable with Al-triethyl (under standard extraction conditions) for at least 70% in moles, and after the extraction it has a surface area of at least 20 $m^2/g$.

Said catalysts comprise, as a co-catalyst, an Al-trialkyl compound to which is added an electron-donor compound (external donor) having the property of not causing complexing reactions with the Al-triethyl detectable by potentiometric titration under specific reaction conditions. The above mentioned electron-donors comprise silicon compounds having Si—OR bonds; 2,2,6,6-tetramethylpiperidine, 2,2,5,5-tetramethylpyrrolidine, Al-diethyl-2,2,6,6-tetramethylpiperidide, Al-dichloromonophenoxy, and other compounds.

GB-A-2 134 911 and GB-A-2 130 225 describe catalysts for polyolefins supported on magnesium halides and comprising combinations of two internal donors, one selected from particular classes of silicon compounds, and the other from ketones.

According to GB-A- 2 130 255, the external donor (i.e., the one added to the supported catalyst component together with the Al-alkyl compound) can also be a ketone. However, the comparative examples of said patent applications show that when only the ketone is present in the internal donor, the performance of the catalysts is unsatisfactory both in terms of stereospecificity and productivity.

Japanese patent application Kokai 61-231008 describes catalysts supported on magnesium halide where the internal donor is selected from the diketones. The examples show that by using the diketones described in the above mentioned patent application one can obtain high levels of stereospecificity and productivity. However, the comparative examples show that the catalysts prepared with the method described in the examples have a high productivity, and above all an unusually high stereospecificity even without the internal donor.

In fact, the propylene homopolymer obtained in comparative example 1, where no internal donor is used, has a total isotactic index (I.I.) of 91.2%. The above performances are not at all typical of the most common catalysts for industrial use, which in the absence of internal donor, give an isotactic index not greater than 85% to 88%, particularly when the external donor used is a silane containing at least one Si—OR, Si—OCOR or $SiNR_2$ bond, where R is a hydrocarbon radical.

The above can be found, for example, in published European patent application 45975.

Now the Applicant has found that it is possible to obtain satisfactory performances, both in terms of catalyst productivity and stereospecificity in the polymerization of olefins, by using a new class of diketones as internal donors, even in the case of catalysts, which, in the absence of an internal donor, produce a propylene homopolymer having an isotactic index which does not exceed 88%. This result is regarded as unexpected, inasmuch as the ketones specifically described in the known art, and particularly in application Kokai 61-231008, as will be shown in the Comparative Examples, are not capable of improving the performance of catalysts which, in the absence of an internal donor, produce a propylene homopolymer having an isotactic index which does not exceed 88%.

Therefore, the present invention provides a solid catalyst component for the polymerization of $C_2-C_8$ alpha olefins which comprises a magnesium halide in active form, and, supported thereon, a titaniumhalide or titanium halogen alcoholate, and an electron-donor compound selected from the 1,3-diketones of formula:

wherein the radicals R are the same or different, the radicals R' are the same or different, and R and R' are $C_1-C_{20}$ alkyl, $C_3-C_{20}$ cycloalkyl, $C_6-C_{20}$ aryl, $C_7-C_{20}$ arylalkyl or alkylaryl radicals or hydrogen, with the proviso that at least one of the R radicals is not hydrogen and can be bonded with the other R radical to form a cyclic structure, and at least one of the R' radicals, which are not bonded to one another to form a cyclic structure, is a branched alkyl, cycloalkyl or aryl radical, or is bonded to one or both R radicals to form a cyclic structure, said 1,3-diketones having the property of being fixed on the catalyst component, when said catalyst component is prepared using a standard method, in quantities that will cause the molar ratio between said 1,3-diketones and the titanium supported on said catalyst component to be higher than or equal to 0.1.

The preferred 1,3-diketones are those of formula (I) wherein the R and R' radicals are not bonded to form cyclic structures.

The above mentioned standard method of preparation of the catalyst component consists of dealcoholating, while increasing the temperature from 50° C. to 100° C., $MgCl_2 \cdot 3C_2H_5OH$ spherical particles having a maximum diameter smaller than or equal to 50 µm, until an adduct of formula $MgCl_2 \bullet 2.1 C_2H_5OH$ is obtained. Said adduct is then contacted at 0° C. with an excess of $TiCl_4$, the entire product is brought to 70° C. and the diketone is added at a $MgCl_2$/ketone molar ratio of 6. The product is caused to react for 2 hours at 100° C., the TiCl₄ is removed, an excess of TiCl₄ is newly added and reacted for one hour at 120° C., then the solid is filtered and washed at 60° C. with heptane until all chlorine ions have been removed from the filtrate.

As previously stated, the diketones defined above are particularly effective in improving the performance of the supported catalyst components that, in the absence of electron-donors supported on said catalyst components, can produce, when used in polymerization, propylene homopolymer having an isotactic index not greater than 88%. Therefore, the above mentioned catalyst components are preferred for the purpose of the present invention. Preferred examples of 1,3-diketones of formula (I) are those having the formula:

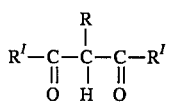
(II)

wherein at least one of the $R'$ radicals, equal or different, is a branched $C_3$–$C_{20}$, preferably $C_3$–$C_9$ alkyl radical having a tertiary or quaternary carbon atom bonded to the carbonyl, or is a $C_3$–$C_{18}$ cycloalkyl or $C_6$–$C_{18}$ aryl radical, and the other $R'$ radical is as defined above or is a $C_1$–$C_{20}$ alkyl, $C_4$–$C_{20}$ cycloalkyl, or $C_7$–$C_{20}$ arylalkyl radical; R is a $C_1$–$C_{12}$ alkyl, $C_3$–$C_{12}$ cycloalkyl, $C_6$–$C_{12}$ aryl, or $C_4$–$C_{12}$ cycloalkylalkyl, preferably $C_1$–$C_{12}$, more preferably $C_1$–$C_6$ linear alkyl radical; or at least one of the $R'$ radicals is bonded to the R radical to form a cyclic structure. The preferred ones, however, are the 1,3-diketones of formula (II) wherein the R and $R'$ radicals are not bonded to form cyclic structures.

In the definition of formulas (I) and (II) are included the cases wherein the alkyl, cycloalkyl, cycloalkylalkyl radicals and the alkyl portion of the arylalkyl radicals contain one or more unsaturations, the cases wherein the cycloalkyl, cycloalkylalkyl, aryl and arylalkyl radicals are substituted, with alkyls for example, and the cases wherein one or more of the categories of radicals described above contain one or more heteroatoms such as N, P, S, O, Cl, F.

Particularly preferred are the 1,3-diketones of formula (II) wherein R and $R'$ are selected from: methyl, ethyl, n-propyl, isopropyl, allyl, n-butyl, isobutyl, sec-butyl, tertbutyl, 1-methylbutyl, n-pentyl, isopentyl, 1-ethylpropyl, 1,1-dimethylpropyl, cyclopentyl, cyclohexyl, phenyl, cyclohexylmethyl, p-methylphenyl.

Specific examples of 1,3-diketones of formula (II) are: 3-isopropyl-5-methyl-2,4-hexanedione; 3-isobutyl-5-methyl-2,4-hexanedione; 3-tert-butyl-5-methyl-2,4-hexanedione; 3-cyclohexyl-5-methyl-2,4-hexanedione; 2-methyl-4-isopropyl- 3,5-heptanedione; 2-methyl-4-isopentyl-3,5-heptanedione; 2 -methyl-4-cyclohexyl-3,5-heptanedione; 2-methyl-4-phenyl-3,5 -heptanedione; 2,4,6-trimethyl-3,5-heptanedione; 2,6-dimethyl- 4-ethyl-3,5-heptanedione; 2,6-dimethyl-4-butyl-3,5-heptanedione; 2,6-dimethyl-4-isopropyl-3,5-heptanedione; 2,6 -dimethyl-4-isobutyl-3,5-heptanedione; 2,6-dimethyl-4 -cyclopentyl-3,5-heptanedione; 2,6-dimethyl-4-tert-butyl-3,5-heptanedione; 2,6-dimethyl-4-allyl-3,5-heptanedione; 2,6-dimethyl-4-phenyl- 3,5-heptanedione; 2,2,4,6-tetramethyl-3,5-heptanedione; 2,2,6-trimethyl-4-ethyl-3,5-heptanedione; 2,2,6-trimethyl-4 -butyl-3,5-heptanedione; 2,2,6-trimethyl-4-isopropyl-3,5-heptanedione; 2,2,6-trimethyl-4-isobutyl-3,5-heptanedione; 2,2,6-trimethyl-4-isopentyl-3,5-heptanedione; 2,2,6-trimethyl- 4-cyclohexyl-3,5-heptanedione; 2,2,6-trimethyl-4-tert-butyl- 3,5-heptanedione; 1-phenyl-3-ethyl-5-methyl-2,4-hexanedione; 2,2,6-trimethyl-4 -allyl-3,5-heptanedione; 2,2,6-trimethyl-4-phenyl-3,5-heptanedione; 2,2,4,6-tetramethyl-3,5-octanedione; 2,2,6 -trimethyl-4-ethyl-3,5-octanedione; 2,2,6-trimethyl-4-butyl- 3,5-octanedione; 2,2,6-trimethyl-4-isobutyl-3,5-octanedione; 3,7-dimethyl-5-isopropyl-4,6-nonanedione; 3,7-dimethyl-5 -isobutyl-4,6-nonanedione; 3,5,5-trimethyl-2,4-hexanedione; 3-ethyl-5,5-dimethyl-2,4-hexanedione; 3-isopropyl-5,5 -dimethyl-2,4-hexanedione; 3-isobutyl-5,5-dimethyl-2,4-hexanedione; 3-tert-butyl-5,5-dimethyl-2,4-hexanedione; 2,2-dimethyl-4 -isopentyl-3,5-heptanedione; 2,2-dimethyl-4-cyclohexyl-3,5-heptanedione; 2,2-dimethyl-4-phenyl-3,5-heptanedione; 2,2,7 -trimethyl-4-ethyl-3,5-octanedione; 2,2,7-trimethyl-4-butyl- 3,5-octanedione; 2,2,7-trimethyl-4-isopropyl-3,5-octanedione; 2,2,7-trimethyl-4-tert-butyl-3,5-octanedione; 2,2,7-trimethyl- 4-cyclopentyl-3,5-octanedione; 2,2,4,6,6-pentamethyl-3,5-heptanedione; 2,2,6,6-tetramethyl-4-ethyl-3,5-heptanedione; 2,2,6,6-tetramethyl-4-propyl-3,5-heptanedione; 2,2,6,6 -tetramethyl-4-butyl-3,5-heptanedione; 2,2,6,6-tetramethyl-4 -hexyl-3,5-heptanedione; 2,2,6,6-tetramethyl-4-isopropyl-3,5-heptanedione; 2,2,6,6-tetramethyl-4-isobutyl-3,5-heptanedione; 2,2,6,6-tetramethyl-4-isopentyl-3,5-heptanedione; 2,2,6,6 -tetramethyl-4-cyclopentyl-3,5-heptanedione; 2,2,6,6 -tetramethyl-4-cyclohexyl-3,5-heptanedione; 2,2,6,6 -tetramethyl-4-tert-butyl-3,5-heptanedione; 2,2,6,6 -tetramethyl-4-phenyl-3,5-heptanedione; 2,2,6,6-tetramethyl-4 -allyl-3,5-heptanedione; 4,8-dimethyl-6-isopropyl-5,7-undecanedione; 4,8-dimethyl-6-isobutyl-5,7-undecanedione; 2,2,6-trimethyl-4-ethyl-3,5-nonanedione; 2,2,6-trimethyl-4 -butyl-3,5-nonanedione; 2,2,6-trimethyl-4-isopropyl-3,5-nonanedione; 3,7-diethyl-5-isopropyl-4,6-nonanedione; 3,7 -diethyl-5-isobutyl-4,6-nonanedione; 3,7-diethyl-5-tert-butyl- 4,6-nonanedione; 3,3,5,7,7-pentamethyl-4,6-nonanedione; 3,3,7,7-tetramethyl-5-ethyl-4,6-nonanedione; 3,3,7,7 -tetramethyl-5-isobutyl-4,6-nonanedione; 3,3,7,7-tetramethyl-5 -allyl-4,6-nonanedione; 1,3-dicyclohexyl-2-isobutyl-1,3-propanedione; 1,1-dibenzoyl-ethane; 1,1-dibenzoyl-2-methylpropane; 1,1-dibenzoyl-2,2-dimethyl-propane; 1,1-dibenzoyl-2 -methyl-butane; 1,1-dibenzoyl-3-methyl-butane; 1,1-di(4 -toluyl)-ethane.

Other examples of 1,3-diketones of formula (I) are those having the formula:

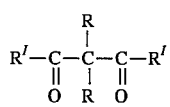
(III)

wherein the R and $R'$ radicals are the same or different and are selected from $C_1$–$C_{20}$ alkyl, $C_3$–$C_{20}$ cycloalkyl, $C_6$–$C_{20}$ aryl, $C_4$–$C_{20}$ cycloalkylalkyl, or $C_7$–$C_{20}$ arylalkyl radicals, or the R radicals are bonded to each other to form a cyclic structure, provided that at least one of the $R'$ radicals is a branched alkyl radical, preferably having a tertiary or quaternary carbon atom bonded to the carbonyl, cycloalkyl or aryl, or that at least one of the $R'$ radicals is bonded with one or both R radicals to form a cyclic structure. The preferred 1,3-diketones are those of formula (III) wherein the R and $R'$ radicals are not bonded to form a cyclic structure.

In the definition of formula (III) are included the cases where the alkyl, cycloalkyl, cycloalkylalkyl radicals and the alkyl portion of the arylalkyl radicals contain one or more unsaturations, the cases wherein the cycloalkyl, cycloalkylalkyl, aryl and arylalkyl radicals are substituted, with alkyls for example, and the cases wherein one or more of the categories of radicals described above contain one or more heteroatoms such as N, P, S, O, Cl, F.

Particularly preferred are the 1,3-diketones of formula (III) where R and R' are selected from: methyl, ethyl, n-propyl, isopropyl, allyl, n-butyl, isobutyl, sec-butyl, tert-butyl, n-pentyl, isopentyl, cyclohexyl, phenyl, p-methylphenyl, benzyl, 2,2-dimethylpropyl.

Specific examples of 1,3-diketones of formula (III) are: 3-isopropyl-3,5-dimethyl-2,4-hexanedione; 3-ethyl-3-isobutyl-5-methyl-2,4-hexanedione; 3,3,5-trimethyl-2,4-hexanedione; 2,4,4,6-tetramethyl-3,5-heptanedione; 2,4,6-trimethyl-4-ethyl-3,5-heptanedione; 2,6-dimethyl-4-ethyl-4-butyl-3,5-heptanedione; 2,4,6-trimethyl-4-isopropyl-3,5-heptanedione; 2,4,6-trimethyl-4-isobutyl-3,5-heptanedione; 2,2,4,6-tetramethyl-4-ethyl-3,5-heptanedione; 2,2,6-trimethyl- 4,4-diethyl-3,5-heptanedione;2,2,6-trimethyl-4-butyl-4-ethyl- 3,5-heptanedione; 2,2,4,6-tetramethyl-4-isopropyl-3,5-heptanedione; 2,2,4,6-tetramethyl-4-isobutyl-3,5-heptanedione; 2,2,6-trimethyl-4-ethyl-4-isopentyl-3,5-heptanedione; 2,2,6 -trimethyl-4-ethyl-4-cyclohexyl-3,5-heptanedione; 2,2,4,6 -tetramethyl-4-allyl-3,5-heptanedione; 2,2,4,6-tetramethyl-4 -phenyl-3,5-heptanedione; 3,3,5,5-tetramethyl-2,4-hexanedione; 3-ethyl-3,5,5-trimethyl-2,4-hexanedione; 3-ethyl-3-isopropyl- 5,5-dimethyl-2,4-hexanedione; 3-isobutyl-3,5,5-trimethyl-2,4-hexanedione; 3-tert-butyl-3,5,5-trimethyl-2,4-hexanedione; 2,2,4,4,6,6-hexamethyl-3,5-heptanedione; 2,2,4,6,6 -pentamethyl-4-ethyl-3,5-heptanedione; 2,2,4,6,6-pentamethyl-4 -propyl-3,5-heptanedione; 2,2,6,6-tetramethyl-4-ethyl-4-butyl- 3,5-heptanedione; 2,2,4,4,6-pentamethyl-3,5-octanedione; 2,2,4,6-tetramethyl-4-ethyl-3,5-octanedione; 3,3,5,5,7 -pentamethyl-4,6-nonanedione; 3-isopropyl-3,5,5-trimethyl-2,4-hexanedione; 2,2,4-trimethyl-4-ethyl-3,5-heptanedione; 2,2,4,4-tetramethyl-3,5-octanedione; 2,2,4,4,7,7-hexamethyl- 3,5-octanedione; 2,2,4,6,6-pentamethyl-4-benzyl-3,5-heptanedione; 2,2,4,6-tetramethyl-4-ethyl-3,5-heptanedione; 2,2,4,4,6-pentamethyl-3,5-heptanedione; 3-isobutyl-3,5 -dimethyl-2,4-hexanedione; 2,4-dimethyl-4-isobutyl-3,5-heptanedione; 2,2-dibenzoylpropane; 2,2-dibenzoyl-butane; 3,3-dibenzoyl-pentane; 2,2 -dibenzoyl-3-methyl-butane; 2,2-dibenzoyl-4-methyl-pentane; 2,2-dibenzoyl-1-phenyl-propane; 4,4-dibenzoyl-1-pentene; 2,2 -di(4-toluyl)-propane.

The 1,3-diketones are prepared with known methods, for example starting from the corresponding diketones not substituted in position between the two carbonylic groups, which are alkylated by reaction with the corresponding alkyl halide (such as methyl iodide, for example) in the presence of a base such as NaH, $K_2CO_3$, tert-butyl-O-K, or by Claisen condensation starting from a monoketone and an acylic chloride, or an anhydride, or an ester, which are caused to react in the presence of a base (such as NaH) or an acid (such as $BF_3$).

Also the preparation of the catalyst components comprising the diketones of formula (I) can be carried our according to various methods.

As a way of example, the magnesium halide (used in the anhydrous state containing less that 1% water), the titanium compound and the diketone are milled together under conditions which cause activation of the magnesium halide. The milled product is then treated one or more times with $TiCl_4$ in excess at a temperature ranging from 80° to 135° C. and is consequently washed repeatedly with a hydrocarbon (hexane) until all chlorine ions have disappeared.

According to another method, the anhydrous magnesium halide is preactivated following known methods and then reacted with an excess of $TiCl_4$ containing the diketone in solution. In this case too one operates at a temperature ranging from 80° to 135° C. The treatment with $TiCl_4$ is optionally repeated and the solid is then washed with hexane to eliminate all traces of nonreacted $TiCl_4$.

According to another method a $MgCl_2$.nROH adduct (specifically in spherical particle form) wherein n usually ranges from 1 and 3, and ROH is an alcohol, such as ethanol, butanol, or isobutanol for example, is reacted with an excess of $TiCl_4$ containing the diketone in solution. The temperature ranges generally from 70° to 120° C. After reaction, the solid is caused to react once more with $TiCl_4$, then it is separated and washed with a hydrocarbon until all chorine ions have disappeared.

According to another method, magnesium alcoholates and chloroalcoholates (the chloroalcoholate prepared specifically as described in U.S. Pat. No. 4,220,554) are caused to react with $TiCl_4$ in excess containing the diketone in solution, operating in this case also under the reaction conditions described above.

According to yet another method, complexes of magnesium halides with titanium alcoholates ( the $MgCl_2.2Ti(OC_4H_9)_4$ complex is a typical example) are caused to react, in a hydrocarbon solution, with $TiCl_4$ in excess containing the diketone in solution. The solid product obtained is again caused to react with an excess of $TiCl_4$ and then separated and washed with hexane. The reaction with $TiCl_4$ is conducted at a temperature ranging from 80° and 120° C.

According to a variation, the complex between $MgCl_2$ and titanium alcoholate is reacted in a hydrocarbon solution with methyl-hydropolysiloxane. The solid product is separated and reacted at 50° C. with silicon tetrachloride containing the diketone in solution. The solid is then reacted with $TiCl_4$ in excess operating at temperatures ranging from 80° to 100° C.

Finally, it is possible to cause porous resins to react with $TiCl_4$ in excess and containing the diketone in solution, such as partially cross-linked styrene-divinylbenzene in spherical particle form, or porous inorganic oxides such as silica and alumina, impregnated with solutions of magnesium compounds or complexes soluble in organic solvents.

The porous resins which can be used are described in published European patent application 344755.

The reaction with $TiCl_4$ is carried out at 80°–100° C. After separating the excess $TiCl_4$, the reaction is repeated and the solid is then washed with a hydrocarbon.

The molar ratio between $MgCl_2$ and diketone used in the above mentioned reactions usually ranges from 2:1 to 12:1.

The diketone is fixed on the magnesium halide in a quantity generally ranging from 1 to 20% molar.

In the catalyst components the Mg/Ti ratio generally ranges from 30:1 to 4:1; in the components supported on resin or on inorganic oxides the ratio is different, and it usually ranges from 20:1 to 2:1.

The titanium compounds that can be used for the preparation of the catalyst components are the halides and the halogen alcoholates. The titanium tetrachloride is the preferred compound.

Satisfactory results are obtained also with titanium trihalides, in particular $TiCl_3$ HR, $TiCl_3$ ARA, and with halogen alcoholates such as $TiCl_3OR$ where R is a phenyl radical.

The reactions mentioned above bring about the formation of magnesium halide in active form. Reactions which bring about the formation of magnesium halide in active form starting from magnesium compounds different than the halides are well known in the literature.

The active form of the magnesium halides in catalyst components may be recognized by the fact that in the X-ray spectrum of the catalyst component is no longer present the major intensity reflection which appears in the spectrum of the non activated magnesium halides (with surface area less than 3 m²/g), but instead there is a halo with the maximum intensity shifted with respect to the position of the major intensity reflection, or by the fact that the major intensity reflection shows a decrease in intensity and a half-peak width at least 30% bigger than the major intensity reflection which appears in the spectrum of the nonactivated magnesium halide.

The most active forms are those where the halo appears in the spectrum of the X-ray of the solid catalyst component.

Among the magnesium halides, the chloride is the preferred compound. In the case of the most active forms of magnesium chloride, the X-ray spectrum of the catalyst component shows a halo instead of the reflection which in the spectrum of the chloride appears at a distance of 2.56 Å.

Preferably, the solid catalyst components containing the diketones of formula (I) have a surface area greater than 30–40 m²/g, in particular ranging from 100 to 300 m²/g. The solid catalyst components containing said diketones of formula (I) form, by reaction with Al-alkyl compounds, catalysts which can be used in the polymerization of $CH_2$=CHR olefins, wherein R is hydrogen or an alkyl radical with 1–8 carbon atoms, or an aryl radical, or a blend of said olefins with one another and/or with diolefins.

In particular, the Al-Alkyl compounds used are selected among the Al-trialkyls, such as Al-triethyl, Al-triisobutyl, Al-tri-n-butyl and linear or cyclic Al-Alkyl compounds containing two or more Al atoms, bonded to one another by way of O, or N atoms or $SO_4$ and $SO_3$ groups.

Examples of these compounds are:

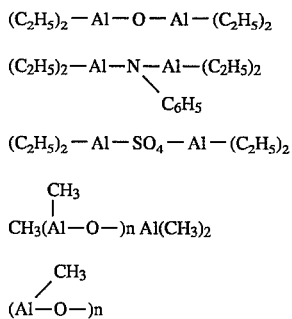

wherein n is a number from 1 to 20.

The Al-alkyl compound is used in an Al/Ti ratio generally ranging from 1 to 1000.

In the case of polymerization of propylene and higher α-olefins the trialkyl compounds can be used in blends with Al-alkyl halides such as $AlEt_2Cl$ and $Al_2Et_3Cl_3$.

In the case of stereoregular polymerization of olefins, if an external electron-donor compound is added to the Al-alkyl the molar ratio between the Al-alkyl compound and the electron-donor compound is from 5:1 to 100:1. Said electron-donor compound is selected, for example, from the external donors described in U.S. Pat. No. 4,522,930, herein incorporated by reference.

Particularly preferred are the electron-donor compounds having the formula:

$R_m SiY_n X_p$ 

wherein R is a $C_1$–$C_{20}$ alkyl, $C_2$–$C_{20}$ alkene, $C_6$–$C_{20}$ aryl, $C_7$–$C_{20}$ arylalkyl, or $C_3$–$C_{20}$ cycloalkyl; Y is an —OR', —OCOR', —NR'$_2$ radical wherein R', equal or different from R, has the same meaning as R; X is a halogen or hydrogen atom, or an —OCOR" or —NR"$_2$ group where R", equal or different from R' has the same meaning as R'; m, n, and p are numbers ranging as follows: m from 0 and 3, n from 1 and 4, and p from 0 and 1; m+n+p equal 4.

Specific examples are: phenyl-alkoxy-silanes such as phenyl-triethoxy- or phenyl-trimethoxy-silane, diphenyl-dimethoxy- and diphenyl-diethoxy-silane, monochlorophenyl-diethoxy-silane; alkyl-alkoxy-silanes such as ethyl-triethoxy-silane, ethyl-triisopropoxy-silane, di-tert-butyl-dimethoxysilane, methyl-cyclohexyl-dimethoxy-silane, dicyclopentyl-dimethoxy-silane, tert-butyl-trimethoxy-silane.

Other electron-donor compounds suitable for use as external donors are selected from 2,2,6,6-tetramethylpiperidine; 2,2,5,5-tetramethylpyrrolidine; 2,2,6,6-tetramethylpiperidide-Al-diethyl; Al-dichloromonophenoxy, and the ethers described in published European patent application 362705, incorporated herein for reference. The above ethers contain two or more ether functions, and have the property of complexing with anhydrous magnesium chloride, under standard conditions, for at least 60 mmoles per 100 g of chloride.

Particularly preferred are the 1,3-diethers of formula:

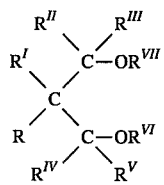

wherein R, $R^I$, $R^{II}$, $R^{III}$, $R^{IV}$ and $R^V$ are the same or different and represent H or linear or branched alkyl, cycloalkyl, aryl, alkylaryl or arylalkyl radicals having 1–18 carbon atoms; $R^{VI}$ and $R^{VII}$ have the same meaning as the radicals from R to $R^V$, except for the hydrogen; provided that at least one of the R and $R^I$ radicals is different from hydrogen, and that when the radicals from $R^I$ to $R^V$ are hydrogen and $R^{VI}$ and $R^{VII}$ are methyl, R is not methyl; and wherein one or more of the R to $R^{VII}$ radicals can be bonded to form a cyclic structure. Examples of said 1,3-diethers are: 2-methyl-2-isopropyl-1,3-dimethoxypropane; 2,2-diisobutyl-1,3-dimethoxypropane; 2-isopropyl-2-cyclopentyl-1,3-dimethoxypropane.

The polymerization of olefins is carried out according to known methods operating in liquid phase comprising the monomer, or monomers, or a solution thereof, in an aliphatic or aromatic hydrocarbon solvent, or in gas phase, or combining liquid and gas polymerization steps.

The (co)polymerization temperature generally ranges from 0° to 150° C., and in particular from 60° to 100° C. The operation takes place at atmospheric temperature or higher. The catalysts can be precontacted with small quantities of olefins (prepolymerization). The prepolymerization improves both the catalyst performance and the morphology of the polymers. The prepolymerization is carried out maintaining the catalyst in suspension in a hydrocarbon solvent (such as hexane or heptane) and the polymerization occurs at a temperature ranging from ambient to 60° C., producing quantities of polymer generally ranging from 0.5 to 3 times the weight of the catalyst. It can also occur in liquid propylene, under the temperature conditions indicated above, thus producing quantities of polymer which can reach up to 100 g per g of catalyst component.

The following examples are given in order to illustrate and not limit the present invention.

EXAMPLE 1

Preparation of
2,2,4,6,6-pentamethyl-3,5-heptanedione

To a solution of 18.3 g of potassium tert-butylate (0.163 moles) in 163 ml of tert-butanol are added dropwise 30 g of dipivaloylmethane (0,163 moles), after which 23.1 g of methyl iodide (0.163 moles) are added slowly. The content is stirred at ambient temperature for 12 hours. The tert-butanol is evaporated to the rotavapor; 20 ml of $H_2O$ are added, and the content is extracted three times with ethyl ether. The ether phases gathered together are anhydrated on $Na_2SO_4$. Distillation is carried out under vacuum with the water pump (20 mm of Hg): the monomethylated product distills at 130° C.

29 g of 2,2,4,6,6-pentamethyl-3,5-heptanedione is obtained (0.146 moles; yield=89.5%).

$^1$H-NMR (CDCl$_3$)

δ (in ppm)

1,2 (s, 18 H, tert-butyl CH$_3$)

1,3 (d, 3H, CH$_3$)

4,5 (dd, 1 H, CH)

EXAMPLE 2

Preparation of
2,2,4,4,6,6-hexamethyl-3,5-heptanedione

To a suspension of 1.6 g of NaH at 80% by weight in 42 ml of anhydrous tetrahydrofurane are added dropwise 8 g of 2,2,4,6,6-pentamethyl-3,5-heptanedione (0.04 moles). The content is stirred at ambient temperature until a homogeneous solution is obtained. 7.7 ml of methyl iodide are then added and a white precipitate forms almost immediately. The content is allowed to agitate at ambient temperature for 12 hours and then the solvent is evaporated. Some water is added (10 ml) and the content is extracted with ether and then anhydrated on $Na_2SO_4$. The ether is evaporated to the rotavapor, isolating a white needle-shaped solid, which is then purified by way of sublimation.

6.5 g of product are obtained (0.031 moles; yield=77.5%).

$^1$H-NMR (CDCl$_3$)

δ (in ppm)

1,2 (s, 18 H, tert-butyl CH$_3$)

1,4 (s, 6 H, CH$_3$ in α to the carbonyls)

EXAMPLE 3

2,2,6,6-tetramethyl-4-ethyl-3,5-heptanedione is prepared operating the same as for Example 1.

1H-NMR (CDCl3)

δ (in ppm)

0,53 (t, 3H, ethyl CH$_3$)

0,84 (s, 18H, tert-butyl CH$_3$)

1,51 (m, 2H, ethyl CH$_2$)

4,06 (t, 1H, CH between the two carbonyls).

EXAMPLE 4

2,2,6,6-tetramethyl-4-allyl-3,5-heptanedione is prepared operating the same as for Example 1.

$^1$H-NMR (CDCl$_3$)

δ (in ppm)

1,18 (s, 9H, tert-butyl CH$_3$)

2,55 (dd, 2H, allyl CH$_2$)

4,45 (t, 1H, CH between the two carbonyls).

5,05 (m, 2H, olefin CH$_2$)

5,6 (m. 1H, olefin CH).

EXAMPLE 5

1,1-dibenzoylethane is prepared operating the same as for Example 1.

1H-NMR (CDCl3)

δ (in ppm)

1,57 (d, 3H, CH$_3$)

5,25 (q, 1H, CH between the two carbonyls)

7,53 (m, 6H, meta-and para-phenyl CH)

7,95 (m, 4H, ortho-phenyl CH)

EXAMPLE 6

2,2-dibenzoylpropane is prepared operating the same as for Examples 1 and 2.

1H-NMR (CDCl3)

δ (in ppm)

1,7 (S, 6H, 2 CH$_3$)

7,2–7,8 (m, 10H, 2 phenyls)

EXAMPLE 7

Preparation of 3,5,5-trimethyl-2,4-hexanedione

In a suspension of 18 g of NaH at 80% by weight in 100 ml of ethyl acetate is added dropwise, while stirring at ambient temperature, a solution comprising 30 g of pivalone (0.3 moles) in 75 ml of anhydrous ethyl ether while maintaining the temperature around 30° C.

400 ml of anhydrous ethyl ether are added in succession in amounts that allow the reaction blend to be stirred, and the content is heated to 40° C. for about 8 hours, then cooled to ambient temperature and the nonreacted sodium hydrate is destroyed with ethanol.

The reaction blend is then cooled to 10° C., and 500 ml of a mixture of water and ice, containing enough HCl to neutralize, are added slowly under nitrogen atmosphere while stirring. The stirring continues until all the solid product has dissolved.

The ether phase is separated and the aqueous phase is reestracted with 100 ml of ethyl ether. The ether extracts gathered together are washed with a solution of sodium bicarbonate, then with water, and they are anhydrated on $Na_2SO_4$.

20.5 g of 5,5-dimethyl-2,4-hexanedione are obtained after distillation under vacuum (at 20 mm Hg, boiling point 70°–71° C.) with a yield=48.1%.

17.4 g of 5,5-dimethyl-2,4-hexanedione (0.123 moles) are added to a solution of 13.8 g of potassium-tert-butylate in 123 ml of tert-butanol.

The content is stirred at ambient temperature for about one hour until the carbanion is formed. The reaction is slightly exothermic and the solution becomes yellowish.

7.7 ml of methyl iodide (0.123 moles) are added dropwise and the content is stirred at ambient temperature. A white precipitate starts to form after about 20 minutes. After three hours the tert-butanol is evaporated in the rotavapor, the residue is suspended in water and extracted with ethyl ether.

The ether phases are anhydrated on Na$_2$SO$_4$. The content is distilled under vacuum (20 mm Hg; boiling point 88.5°–89.5° C.).

17.2 g of 3,5,5-trimethyl-2,4-hexanedione are obtained, with a yield of 89.4%.

$^1$H-NMR (CDCl$_3$) of 5,5-dimethyl-2,4-hexanedione

δ (in ppm)

1,2 (s, 9 H, tert-butyl CH$_3$)

2.1 (s, 3 H, enolic CH$_3$)

2.25 (s, 3 H, ketonic CH$_3$)

3,65 (s, 2 H, ketonic CH$_2$) 5,6 (s, 1 H, enolic olefin CH)

$^1$H-NMR (CDCl$_3$) of 3,5,5-trimethyl-2,4-hexanedione

δ (in ppm)

1,18 (s, 9 H, tert-butyl CH$_3$)

1.33 (s, 3 H, CH$_3$)

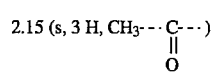

4,1 (q, 1H, CH between the two carbonyls)

COMPARATIVE EXAMPLE 1

2,2,6,6-tetramethyl-4 benzyl-3,5-heptanedione is prepared operating as in Example 1.

$^1$H-NMR (CDCl$_3$)

δ (in ppm)

1,1 (s, 18 H, tert-butyl CH$_3$)

3.1 (d, 2 H, benzyl CH$_2$)

4.75 (t, 1 H, CH between the two carbonyls)

7.2 (m, 5H, phenyl)

EXAMPLES 8–14 AND COMPARATIVE EXAMPLE 2

Preparation of Solid Catalyst Component

Into a 500 ml reactor complete with porous barrier are introduced at 0° C. 225 ml of TiCl$_4$. While stirring one adds, in 15 minutes, 10.3 g of microspheroidal MgCl$_2$●2.1C$_2$H$_5$OH obtained as described below. Once the addition is completed the temperature is brought to 70° C., 9 mmoles of 1,3-diketones are added and the content is heated to 100° C. allowing it to react at this temperature for two hours, after which the TiCl$_4$ is filtered out. 200 ml of TiCl$_4$ are added and the content is allowed to react at 120° C. for one hour, after which it is filtered and washed at 60° C. with anhydrous heptane until all chlorine ions have disappeared from the filtrate.

The microspheroidal MgCl$_2$●2.1C$_2$H$_5$OH adduct is prepared as follows.

48 g of anhydrous MgCl$_2$, 77 g of anhydrous C$_2$H$_5$OH, and 830 ml of kerosene are introduced in a 2 liter autoclave complete with turbine agitator and dip pipe, under inert gas and at ambient temperature,. The content is heated to 120° C. while under agitation, and the adduct is formed between MgCl$_2$ and the alcohol; this adduct then melts and remains mixed to the dispersing agent. A nitrogen pressure of 15 atm is maintained inside the autoclave. The autoclave dip-pipe is externally heated to 120° C. by way of a heating jacket, and it has a 1 mm inside diameter and its length, from end to end of the heating jacket, is 3 meters. The mixture is circulated through the pipe at a speed of 7 m/sec. The dispersion is gathered in a 5 liter flask, under agitation, said flask containing 2.5 liter of kerosene, and being externally cooled by a jacket maintained at the initial temperature of –40° C. The final temperature of the emulsion is 0° C. The spherical solid product that constituted the dispersed phase of the emulsion is separated by settling and filtration, then washed with heptane and dried. All the above operations are carried out in an inert gas atmosphere.

130 g of MgCl$_2$.2,1C$_2$H$_5$OH are obtained in the form of solid spherical particles with a maximum diameter of less than 50 μm. The product is then dealcoholated at temperatures which are gradually increased from 50° C. to 100° C. in nitrogen flow until the alcohol content reaches 2.1 moles per mole of MgCl$_2$.

EXAMPLES 15–21 AND COMPARATIVE EXAMPLE 3

Propylene Polymerization

In a 4 liter stainless steel autoclave equipped with anchor agitator, and previously purged by way of nitrogen flow at 70° C. for 1 hour, are introduced, in propylene flow at 30° C., 80 ml of anhydrous n-hexane containing 15 mg of the solid catalyst component of Examples 8–14 and Comparative example 2, 7 mmoles of AlEt$_3$, and 0.35 mmoles of cyclohexylmethyldimetoxysilane. The autoclave is closed, and 1,7N liters of hydrogen are introduced. The agitator is put in motion, and 1.2 kg of liquid propylene are fed. It is heated to 70° C. in 5 min. and the polymerization is carried out for 2 hours. Finally the nonreacted propylene is removed, the polymer is recovered, dried in a 70° C. oven in nitrogen flow for 3 hours, and then characterized.

Table 1 indicates the 1,3-diketones used and the characteristics of the solid catalyst components obtained.

Table 2 shows the yield in kg of polypropylene/g of catalyst component as well as the characteristics of the polymers obtained.

TABLE 1

| | Preparation | Catalyst component Analysis | | | |
|---|---|---|---|---|---|
| Ex. n. | 1,3-diketone (Ex. n.) | Mg (weight %) | Ti (weight %) | Diketone (weight %) | Diketone/Ti (moles) |
| 8 | 1 | 18.2 | 3.1 | 9.6 | 0.75 |
| 9 | 2 | 20.1 | 4.6 | 3.6 | 0.2 |
| 10 | 3 | 19.8 | 2.9 | 12.3 | 1 |
| 11 | 4 | 19.8 | 3.9 | 3.3 | 0.2 |
| 12 | 5 | 16.7 | 4.8 | 5 | 0.2 |

TABLE 1-continued

| | Catalyst component | | | | |
|---|---|---|---|---|---|
| Preparation | | Analysis | | | |
| Ex. n. | 1,3-diketone (Ex. n.) | Mg (weight %) | Ti (weight %) | Diketone (weight %) | Diketone/Ti (moles) |
| 13 | 6 | 17.5 | 3.6 | 6.1 | 0.3 |
| 14 | 7 | 19.1 | 4.6 | 3.7 | 0.3 |
| Comp. 2 | Comp. 1 | 14.1 | 5.1 | 0.5 | 0.02 |

TABLE 2

| Polymerization | | | | |
|---|---|---|---|---|
| | Catalyst | Polymer | | |
| Ex. n. | component (Ex. n.) | Yield (Kg PP/g Cat) | X.I. (weight %) | MFR (g/10 min) |
| 15 | 8 | 35.6 | 96.6 | 4.3 |
| 16 | 9 | 32.7 | 90.3 | 12.5 |
| 17 | 10 | 31 | 96.8 | 3.1 |
| 18 | 11 | 18 | 92.4 | 6.6 |
| 19 | 12 | 36.1 | 92.3 | 8 |
| 20 | 13 | 24.8 | 90 | 12.4 |
| 21 | 14 | 28.7 | 91.3 | 9.7 |

TABLE 2-continued

| Polymerization | | | | |
|---|---|---|---|---|
| | Catalyst | Polymer | | |
| Ex. n. | component (Ex. n.) | Yield (Kg PP/g Cat) | X.I. (weight %) | MFR (g/10 min) |
| Comp. 3 | Comp. 2 | 23.6 | 85.1 | 10.6 |

X.I. is the isotactic index in xylene at 25° C., i.e., the quantity of polymer which remains insoluble in xylene at 25° C.

MFR is the Melt Flow Rate measured according to ASTM D 1238 L.

The above definitions are also valid for the examples that follow. Moreover, the analysis of the diketone content in the catalyst component is carried out by decomposing the same in ethanol and analyzing the solution obtained by way of gaschromatography, using the internal standard method with a Carlo Erba HRGC 5300 Mega Series gaschromatograph with 25 meters Chrompack CP-SIL 5 CB capillary column.

COMPARATIVE EXAMPLES 4–10

Preparation of the Solid Catalyst Component

The operation is the same as for the preceding examples using the diketones indicated in Table 3.

TABLE 3

| | Catalyst component | | | | |
|---|---|---|---|---|---|
| Preparation | | Analysis | | | |
| Comp. Ex. n. | Diketone | Mg (weight %) | Ti (weight %) | Diketone (weight %) | Diketone/Ti (moles) |
| 4 | I | 17.8 | 7.3 | absent | — |
| 5 | II | 18.5 | 5.0 | 6.5 | 0.4 |
| 6 | III | 13.1 | 6.3 | 0.5 | 0.01 |
| 7 | IV | 17.1 | 6.4 | 4.6 | 0.3 |
| 8 | V | 14.6 | 8 | 0.7 | 0.04 |
| 9 | VI | 15.6 | 7.4 | 0.7 | 0.03 |
| 10 | VII | 16 | 5.2 | absent | — |

Note for Table 3
I = 4,4,4-trifluoro-1-phenyl-1,3-butanedione
II = 1-benzoylacetone
III = 1,2-dibenzoylbenzene
IV = 2,5-hexanedione
V = 1,4-cyclohexanedione
VI = 5,5-dimethyl-1,3-cyclohexanedione
VII = 2-acetyl-1-tetralone

COMPARATIVE EXAMPLES 11–17

Propylene Polymerization

The operation is the same as in preceding examples, using the catalyst components of Comparative examples 4–10.

Table 4 shows the yield in kg of polypropylene/g of catalyst component as well as the characteristics of the polymers obtained.

TABLE 4

| Comp. Ex. n. | Polymerization Catalyst component (Comp. Ex. n.) | Polymer Yield (Kg PP/g Cat) | X.I. (weight %) | MFR (g/10 min) |
|---|---|---|---|---|
| 11 | 4  | 22   | 81.9 | 9.4 |
| 12 | 5  | 26.7 | 87.9 | 8.6 |
| 13 | 6  | 13.8 | 87.3 | 9.2 |
| 14 | 7  | 16   | 86.3 | 14 |
| 15 | 8  | 20.8 | 83.7 | 14 |
| 16 | 9  | 8.1  | 84.7 | 13.6 |
| 17 | 10 | 20   | 86.5 | 14.2 |

EXAMPLE 22

Propylene Polymerization

The operation is the same as in preceding examples, using the catalyst components of Example 8, and instead of the cyclohexylmethyldimethoxysilane, one uses 2-isopropyl-2-isoamyl-1,3-dimethoxypropane in an equal molar quantity.

The result is as follows:

| Yield (KgPP/g Cat.) | X.I. (weight %) | MFR (g/10 min.) |
|---|---|---|
| 28 | 96.8 | 6.2 |

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

We claim:

1. A solid catalyst component for the polymerization of olefins, comprising a magnesium halide in active form and, supported on said magnesium halide, a titanium halide or titanium halogen alcoholate and an electron-donor compound selected from 1,3-diketones of formula:

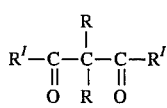

(I)

wherein the radicals R are the same or different, the radicals R' are the same or different, and are not bonded to one another to form a cyclic structure, and R and R' are $C_1-C_{20}$ alkyl, $C_3-C_{20}$ cycloalkyl, $C_6-C_{20}$ aryl, $C_7-C_{20}$ arylalkyl or alkylaryl radicals or hydrogen, with the proviso that at least one of the R radicals is not hydrogen and can be bonded with the other R radical to form a cyclic structure, and at least one of the R' radicals, is a branched alkyl, cycloalkyl or aryl radical, or is bonded to one or both R radicals to form a cyclic structure, said 1,3-diketone being fixed on the catalyst component such that the mole ratio between said 1,3-diketone and the titanium supported on said magnesium halide is higher than or equal to 0.1.

2. The solid catalyst component of claim 1, wherein the magnesium halide is magnesium chloride and the titanium halide is titanium tetrachloride.

3. The solid catalyst component of claim 1, wherein the electron-donor compound is selected from 1,3-diketones of formula:

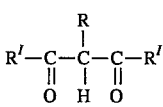

(II)

wherein at least one of the R' radicals is a branched $C_3-C_{20}$ radical having a tertiary or quaternary carbon atom bonded to the carbonyl, or is a $C_3-C_{18}$ cycloalkyl or $C_6-C_{18}$ aryl radical, and the other R' radical is as defined above or is a $C_1-C_{20}$ alkyl, $C_4-C_{20}$ cycloalkyl or $C_7-C_{20}$ arylalkyl radical; R is a $C_1-C_{12}$ alkyl, $C_3-C_{12}$ cycloalkyl, $C_6-C_{12}$ aryl or $C_4-C_{12}$ cycloalkylalkyl radical; or at least one of the R' radicals is bonded to the R radical to form a cyclic structure; or from the 1,3-diketones of formula:

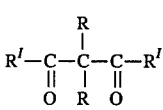

(III)

wherein the R and R' radicals are the same or different and are selected from $C_1-C_{20}$ alkyl, $C_3-C_{20}$ cycloalkyl, $C_6-C_{20}$ aryl, $C_4-C_{20}$ cycloalkylalkyl or $C_7-C_{20}$ arylalkyl radicals, or the R radicals are bonded to each other to form a cyclic structure, provided that at least one of the R' radicals is a branched alkyl, cycloalkyl or aryl radical, or that at least one of the R' radicals is bonded with one or both R radicals to form a cyclic structure.

4. A solid catalyst component for the polymerization of olefins, comprising a magnesium halide in active form and, supported on said magnesium halide, a titanium halide or titanium halogen alcoholate and an electron-donor compound, wherein the electron donor compound is selected from 2,2,4,6,6-pentamethyl-3,5-heptanedione and 2,2,6,6-tetramethyl-4-ethyl-3,5-heptanedione, said electron donor compound being fixed on the catalyst component such that the mole ratio between the electron donor and the titanium supported on said magnesium halide is higher than or equal to 0.1.

5. A catalyst for the polymerization of olefins comprising the product of the reaction between the solid catalyst component of claim 1 and an Al-alkyl compound.

6. Catalyst of claim 5 to which is added an external electron-donor compound.

7. The catalyst of claim 6 wherein the external electron-donor is selected from 2,2,6,6-tetramethylpiperidine, 2,2,5,5-tetramethylpyrrolidine; Al-diethyl-2,2,6,6-tetramethylpiperidide, Al-dichloromonophenoxy, and compounds having the formula:

$$R_mSiY_nX_p$$

wherein R is a $C_1-C_{20}$ alkyl, $C_2-C_{20}$ alkene, $C_6-C_{20}$ aryl, $C_7-C_{20}$ arylalkyl, or $C_3-C_{20}$ cycloalkyl; Y is an —OR', —OCOR', —NR'$_2$ radical wherein R' is the same as or different from R and has the same meaning as R; X is a halogen or hydrogen atom, or an —OCOR" or —NR"$_2$ group wherein R" is the same as or different from R' and has the same meaning as R'; m, n, and p are numbers ranging as follows: m from 0 and 3, n from 1 and 4, and p from 0 and 1; m+n+p equal 4.

8. The catalyst of claim 6, wherein the external electron-donor is a 1,3-diether of formula:

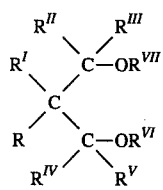

wherein R, $R^I$, $R^{II}$, $R^{III}$, $R^{IV}$ and $R^V$ equal or different, represent hydrogen or linear or branched alkyl, cycloalkyl, aryl, alkylaryl or arylalkyl radicals having 1–18 carbon atoms; $R^{VI}$ and $R^{VII}$ have the same meaning of the radicals from R to $R^V$, except for the hydrogen; provided that at least one of the R and $R^I$ radicals is different from hydrogen, and that when the radicals from $R^I$ to $R^V$ are hydrogen and $R^{VI}$ and $R^{VII}$ are methyl, R is not methyl; and wherein one or more of the R to $R^{VII}$ radicals can be bonded to form a cyclic structure.

* * * * *